United States Patent [19]

Tepic

[11] Patent Number: 5,458,654
[45] Date of Patent: Oct. 17, 1995

[54] SCREW-FIXED FEMORAL COMPONENT FOR HIP JOINT PROSTHESIS

[75] Inventor: Slobodan Tepic, Davos, Switzerland

[73] Assignee: AO-Forschungsinstitut Davos, Davos-Platz, Switzerland

[21] Appl. No.: 92,116

[22] Filed: Jul. 14, 1993

[51] Int. Cl.⁶ ................................... A61F 2/32
[52] U.S. Cl. ................ 623/23; 606/62; 606/69
[58] Field of Search .................. 623/16, 18, 23; 606/62, 67, 69

[56] References Cited

U.S. PATENT DOCUMENTS

| | | | |
|---|---|---|---|
| 4,080,666 | 3/1978 | Fixel | 606/64 X |
| 4,129,903 | 12/1978 | Huggler | 606/67 X |
| 4,530,115 | 7/1985 | Müller et al. | 606/62 |
| 4,775,381 | 10/1988 | Tari et al. | 606/62 |
| 4,827,917 | 5/1989 | Brumfield | 606/64 |
| 4,921,501 | 5/1990 | Giacometti | 623/23 |
| 5,041,114 | 8/1991 | Chapman et al. | 606/62 |
| 5,053,036 | 10/1991 | Perren et al. | 606/69 |
| 5,108,449 | 4/1992 | Gray | 623/23 |
| 5,122,141 | 6/1992 | Simpson et al. | 606/62 |
| 5,167,666 | 12/1992 | Mattheck et al. | 606/62 |

FOREIGN PATENT DOCUMENTS 3725111  2/1989  Germany ................. 606/62

*Primary Examiner*—David Isabella
*Attorney, Agent, or Firm*—Walter C. Farley

[57] ABSTRACT

The femoral component for a hip joint prosthesis has an intramedullary stem having a free distal region, a proximal region extending to a neck for receiving a ball head, a medial side and a lateral side.

The stem has screw holes extending from said lateral side to said medial side for receiving bone screws in the lateral to medial direction for fixation of said stem to the medial cortex. The stem is coupled primarily to the medial cortex of the femur and only secondarily to the cancellous portion of the proximal femur to aid the rotational (torsional) stability of the implant.

7 Claims, 6 Drawing Sheets

# SCREW-FIXED FEMORAL COMPONENT FOR HIP JOINT PROSTHESIS

FIELD OF THE INVENTION

This invention relates to a femoral component for a hip joint prosthesis with an intramedullary stem having a free distal region, a proximal region extending to a neck for receiving a ball head, a medial side and a lateral side.

BACKGROUND ART

Long lasting cementless fixation of the femoral component of the hip joint prosthesis remains an unsolved problem. Efforts to do so by surface treatments of the prosthesis stem that would allow bony ingrowth have not resulted in satisfactory clinical results and the cemented femoral component is still considered a better choice for most patients. Current designs of all stemmed hip prosthesis rely on the load transfer by rod-in-tube configuration. The load on the head of the prosthese results in both axial and transverse forces and bending moments (mostly in the frontal plane, but also, and depending on the particular action of the patient, in other planes, generally torsional loads around the long axis of the stem) which must be transferred to bone.

This leads to stem-bone interactions along the stem, which generally compress the medial cortex proximally and the lateral cortex distally. Due to additional muscle loads on predominantly the greater trochanter, bone undergoes significant deformation and it is very difficult if possible at all, to prevent the movements at the prosthesis-bone interface. Bony ingrowth is thus inhibited, and if, and when it occurs, it is limited to only some areas of the interface. At other places motion persists leading to pain, overall instability of the implant and eventual failure. In some cases of porous (bead) coated stems, the bone has been seen to integrate well on the distal parts of the prosthesis, which in turn produced massive bone loss due to stress-shielding.

SUMMARY OF THE INVENTION

The invention described here solves the problem of stem fixation by coupling the stem primarily to the medial cortex of the femur, and only secondarily to the cancellous portion of the proximal femur for aiding the rotational (torsional) stability. Means of fixation are bone screws locked into the stem to prevent them from wobbling loose in the bone.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

DETAILED DESCRIPTION OF THE INVENTION

Figures 1, 1A:
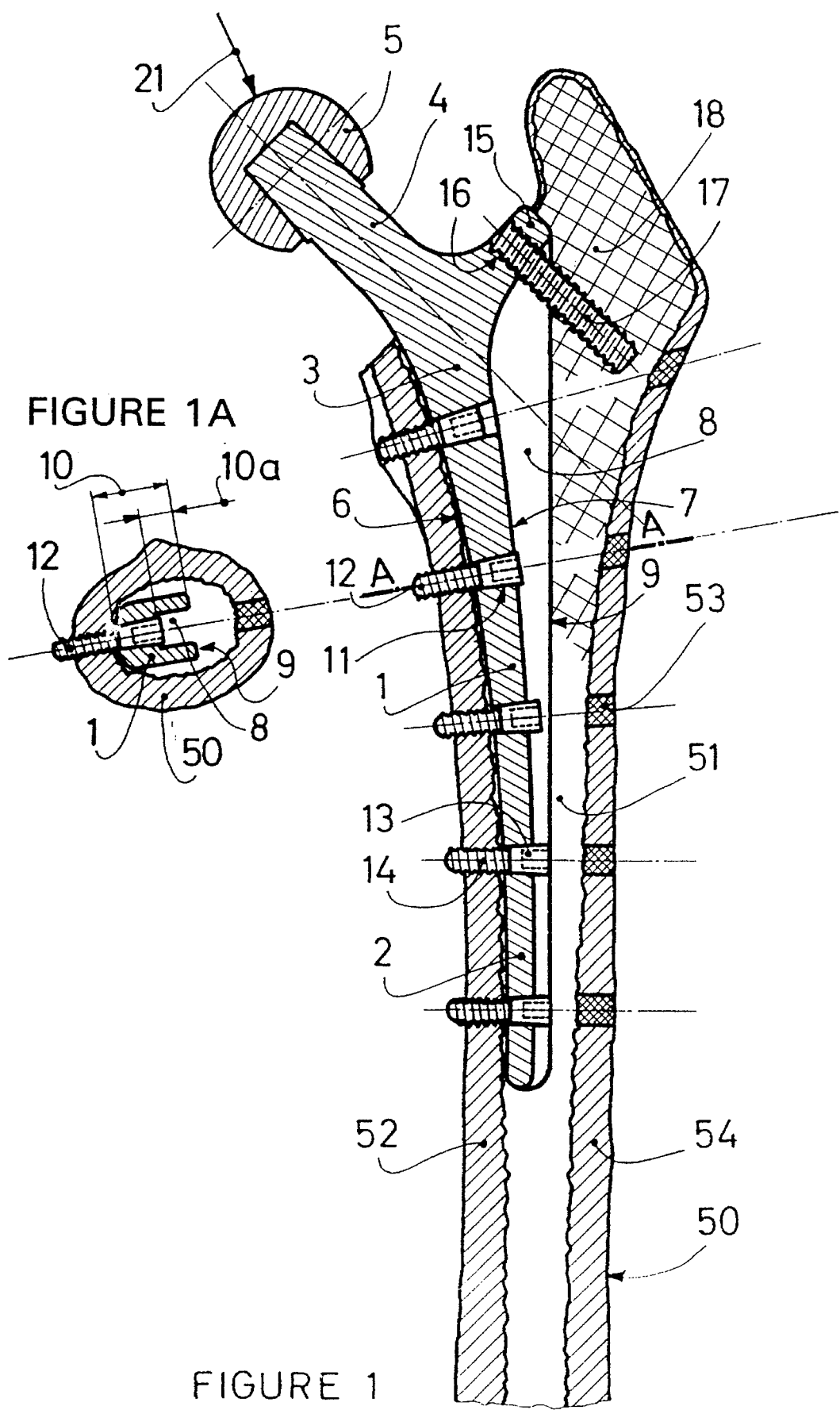
FIG. 1 is a frontal plane section of a femoral component according to the invention.
FIG. 1A is a transverse sectional view along line A—A of FIG. 1.

FIG. 1 shows a frontal section of the left femur 50 with the femoral component of the hip joint prosthesis inserted into the medullary cavity 51 and fixed to the medial cortex 52. The prosthesis basically consists of the stem 1, the neck 4, the trochanteric collar 15 and the ball head 5. The stem 1 is curved to fit the inner wall of the medial cortex 52, from its proximal region 3 to its free distal region 2. The trochanteric collar 15 extends laterally from the proximal region 3 of the stem 1. The neck 4 meets proximal region 3 of the stem 1 at the level of the extension of the trochanteric collar 15. The ball head 5 of the hip joint prosthesis is attached to the neck 4. The stem 1 is fixed to the medial cortex 52 by a number of bone screws 12, which preferably are self-tapping. These are passed through clearance holes 53 drilled in the femur lateral cortex 54. After insertion of the screws 12 the holes 53 may be plugged by cancellous bone plugs to accelerate healing of the holes 53. The bone screws 12 engage the medial cortex 52 by their threaded portion 14. The heads 13 of the bone screws 12 lock in the stem screw holes 11, preferably by means of a shallow taper on the head and in the hole. The details of the taper are disclosed in detail in U.S. Pat. No. 5,151,103 TEPIC et al., which is incorporated herein by reference.

The rigid locking of the bone screws 12 is important for the stability of the construct; extensive trials with a fracture treatment plate utilizing the preferred design described above showed a clear advantage over conventional screw plate systems. By extreme medial placement of the stem 1 within the medullary cavity 51 the force 21 on the ball head 5 of the prosthesis can be supported by mostly shear forces on the bone screws 12. Very little bending is produced on the stem 1 which allows for sufficient strength of the implant even in the presence of the screw holes 11 which cause stress concentration.

The impact of the stress concentration around the stem screw holes 11 can be reduced by cutting a longitudinal groove 8 along the lateral side 9 of the stem 1 as seen in FIG. 1A. Even though some material is removed and the stem cross-section, now U-shaped, is weakened, the stem screw holes 11 end at the groove bottom 7 where bending stresses are lower than at the extremity of the lateral side 9 of the stem 1, i.e. at the endings of the legs of the U-shaped cross-section. Maximum principal stress can be reduced by about 30% with the depth 10a of the groove 8 equal to about 25% of the total width 10 of the U-shaped cross-section.

Maximum compressive stresses on the medial side 6 of the stem 1 are increased by the presence of the groove 8. This, however, is less important since the screw heads 13 are inserted tightly into holes 11 and will reduce the effects of stress concentration to stabilize the stem against out-of-frontal plane components of the joint force 21. The prosthesis collar 15 is provided with a threaded hole 16. An additional screw 17 is threaded through the hole 16 to engage cancellous bone 18 of the greater trochanter.

Figure 2:
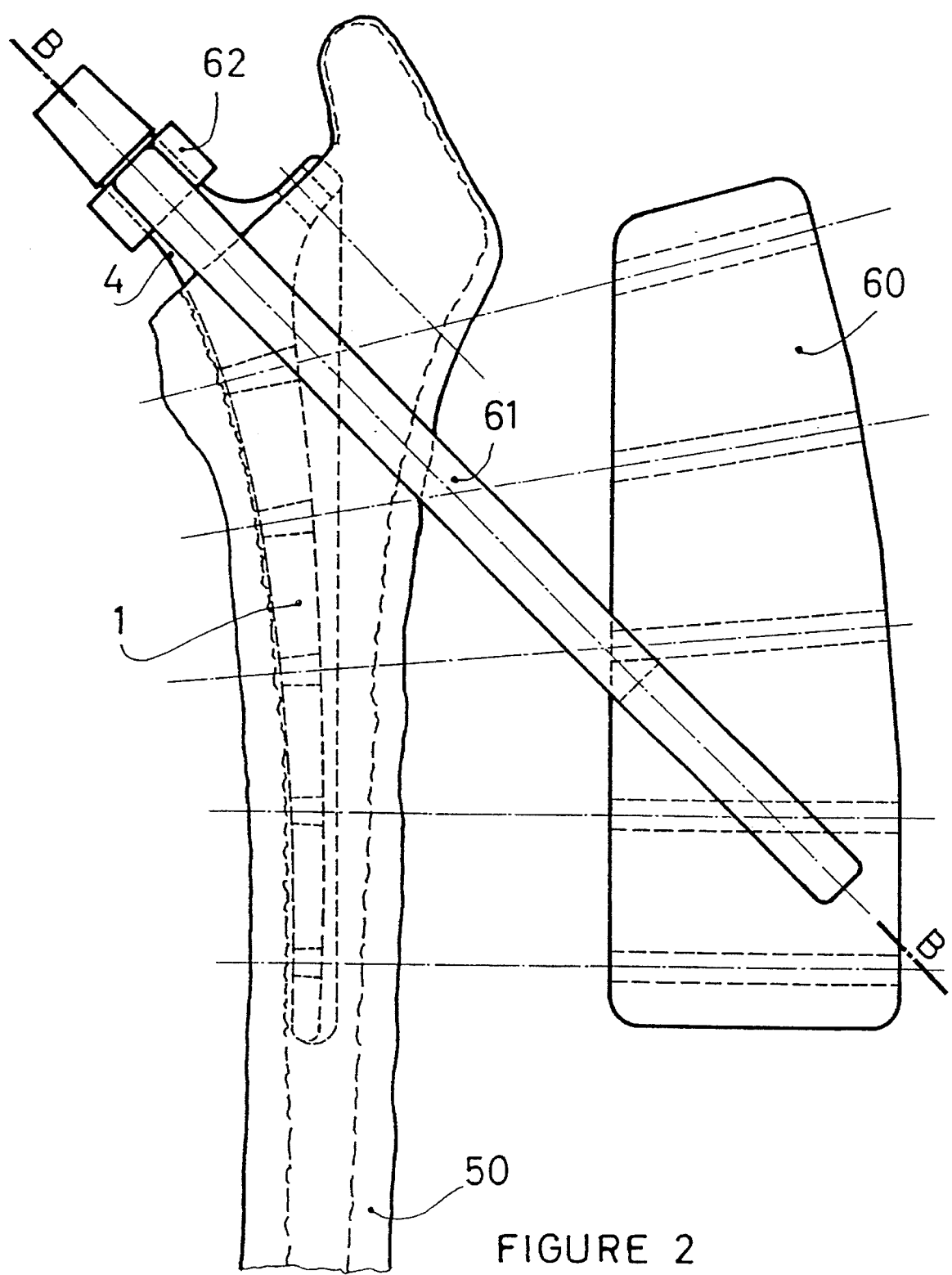
FIG. 2 is a frontal view of a femoral component according to FIG. 1 with a guiding instrument for its insertion.

FIG. 2 shows a guiding instrument used to fix the prosthesis stem 1 into bone 50. A drill guide plate 60 is attached to the neck 4 of the prosthesis via a bridge 61 and a clamp 62.

Figure 3:
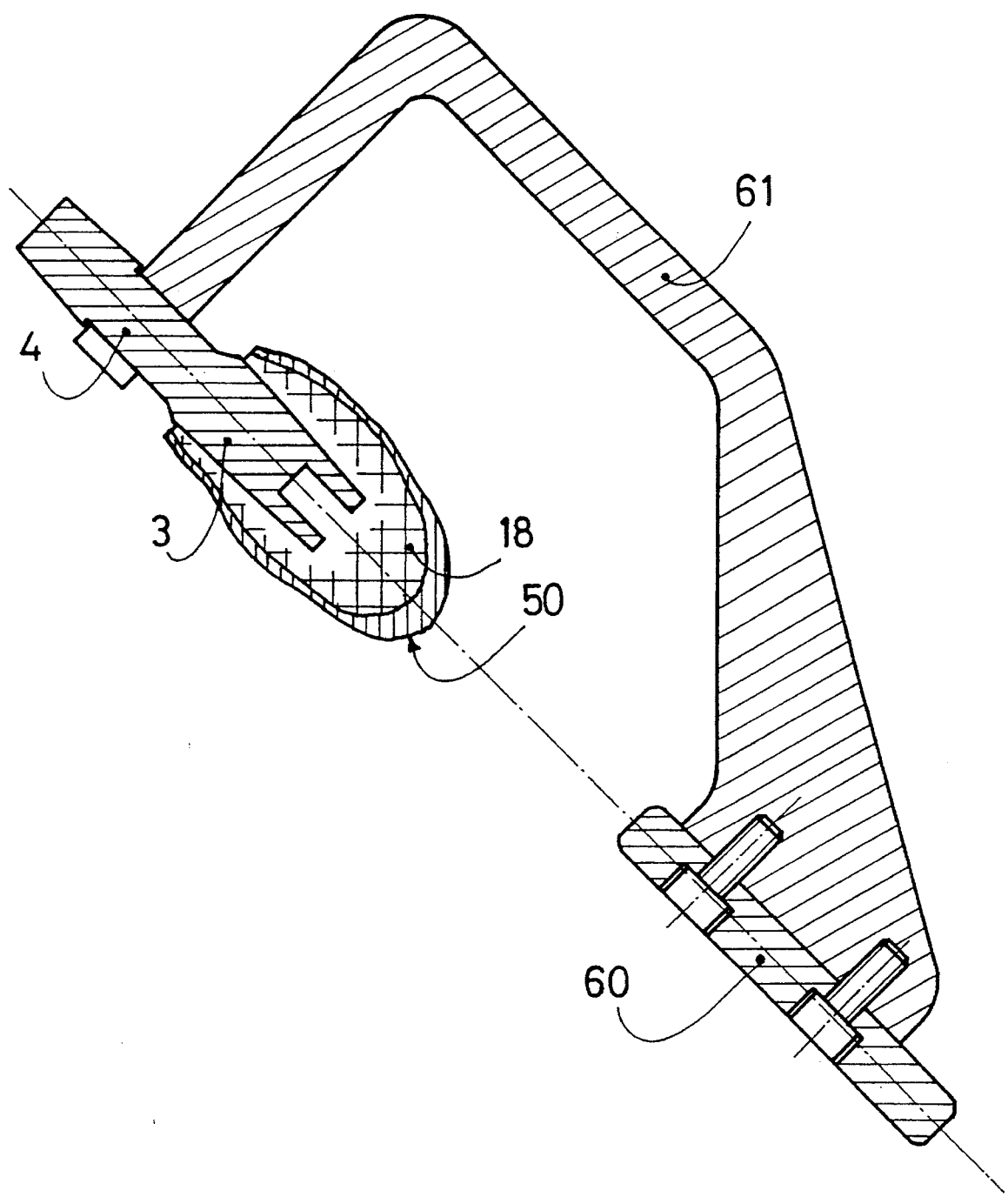
FIG. 3 is a cross section of the guiding instrument of FIG. 2 along the line B—B of FIG. 2.

FIG. 3 shows the section B—B of FIG. 2 where the shape of the bridge 61 is seen more clearly from the top. Its arc is used to clear the tissues surrounding the ]Done 50 and bring the plate 60 into the frontal plane and laterally to the bone.

Figure 4:
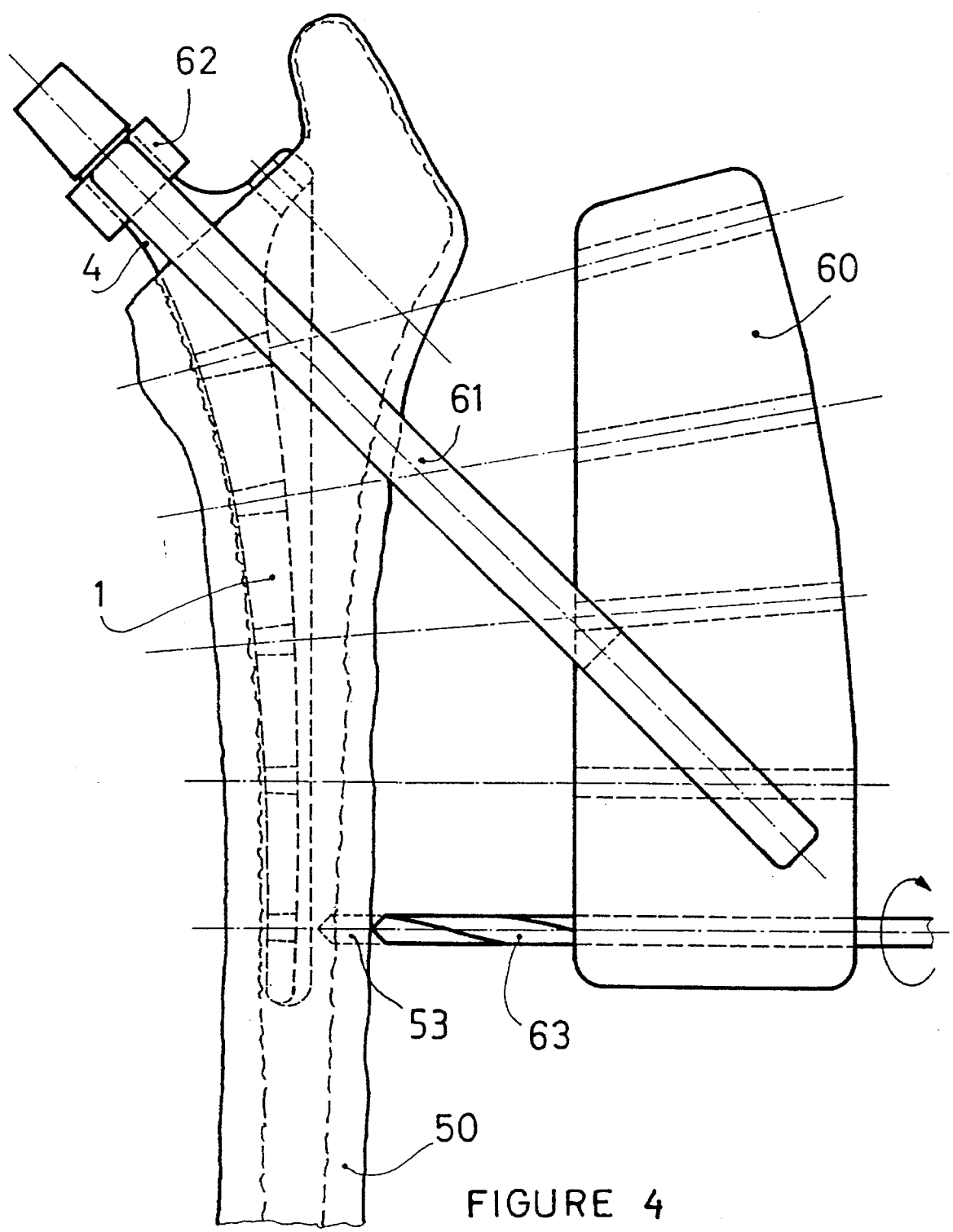
FIG. 4 is a frontal view of the femoral component according to FIG. 2 with a drill inserted in the guiding instrument.
Figure 5:
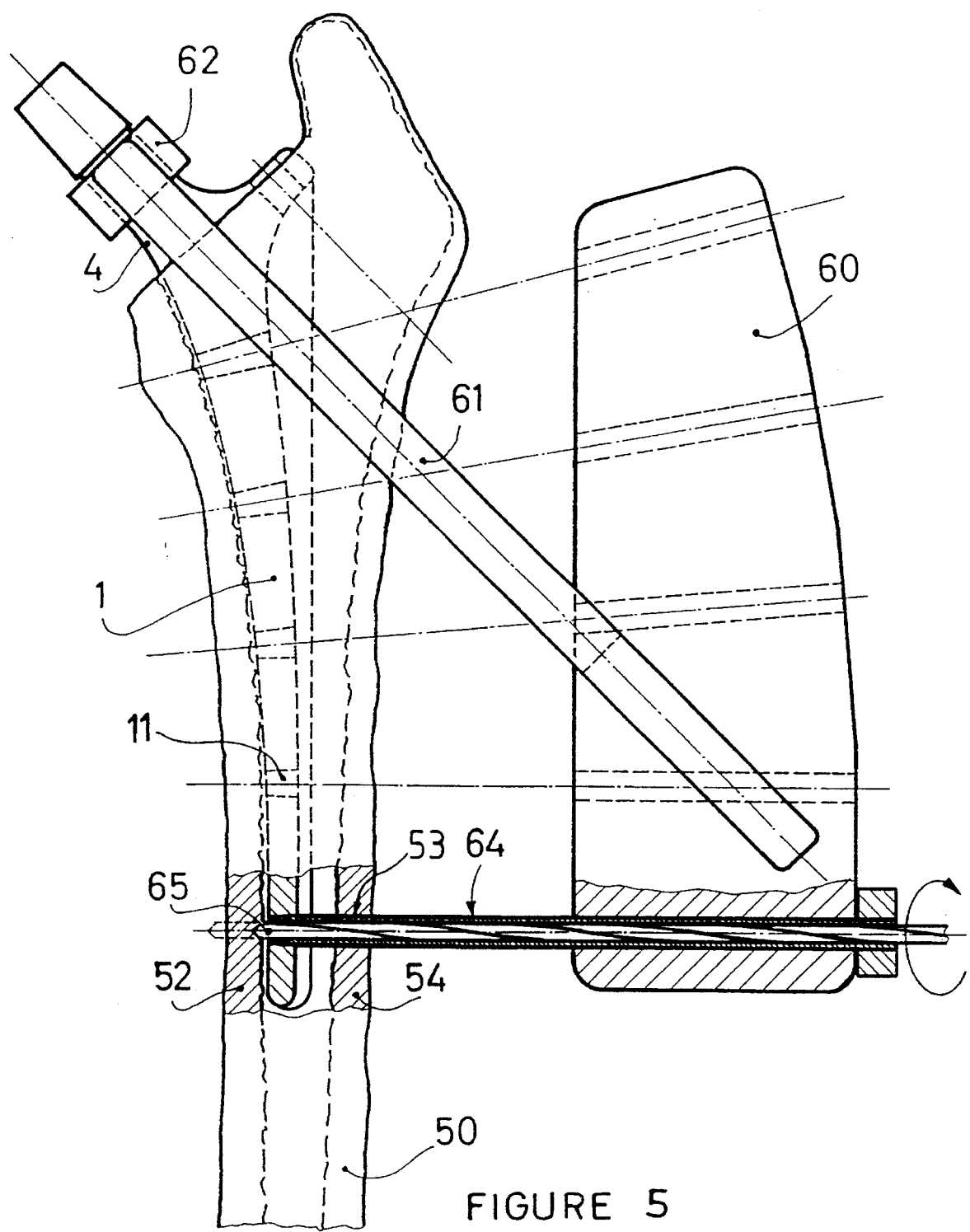
FIG. 5 is a frontal view of the femoral component according to FIG. 2 with a drill guide tube inserted in the guiding instrument.
Figure 6:
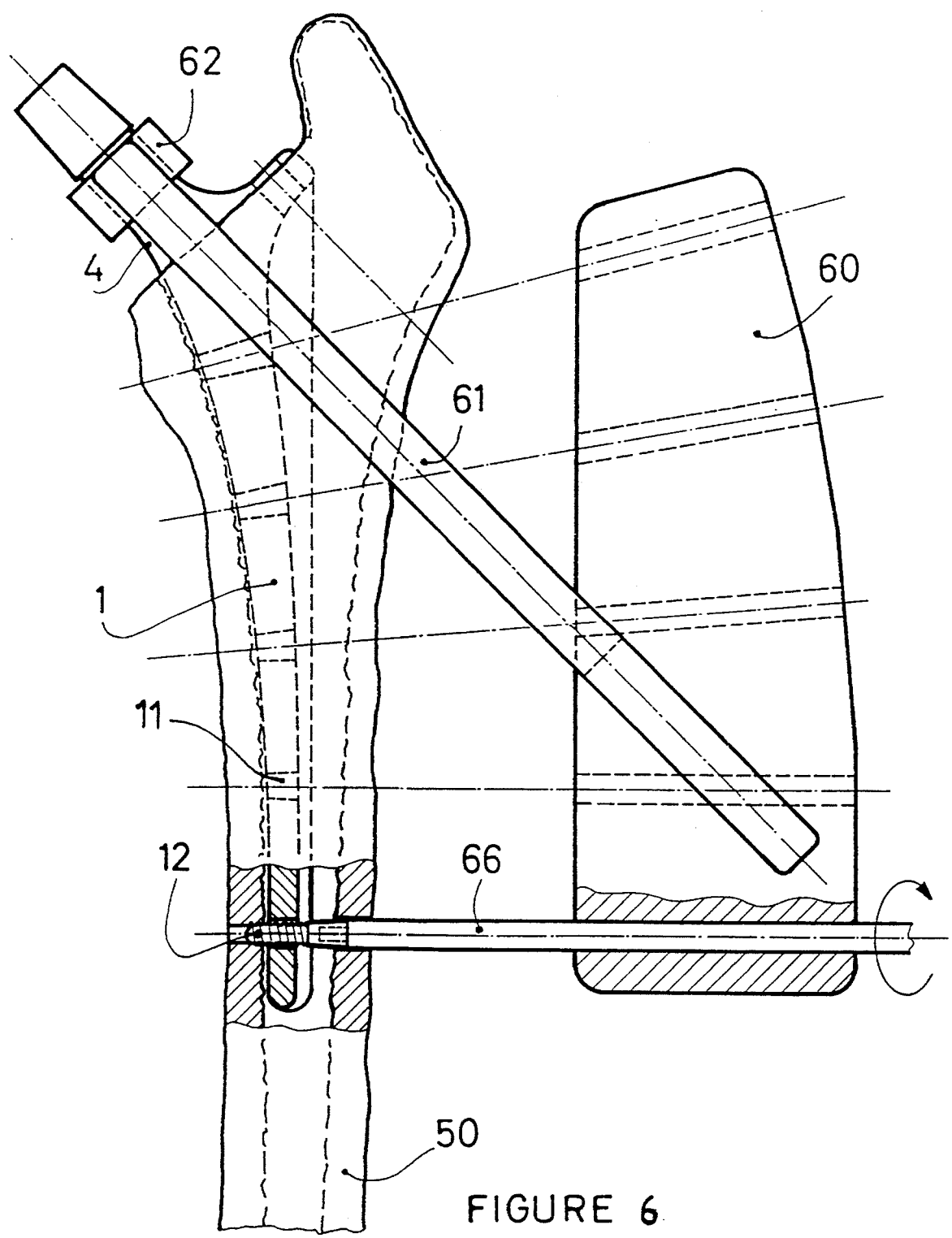
FIG. 6 is a frontal view of the femoral component according to FIG. 2 with a screw driver inserted in the guiding instrument.

FIGS. 4–6 show the basic steps of the fixation procedure. After placement of the stem 1 into bone 50, a drill 63, preferably having a diameter of 5 mm, is used first to drill a hole 53 through the lateral cortex 54 of the bone 50 (FIG. 4). In the second step (FIG. 5) a drill guide tube 64 is passed through the plate 60 and the just-drilled hole 53 in the lateral cortex 54, to engage the conical hole 11 of the stem 1. A smaller drill 65, having a diameter of 3.5 mm, is next used to drill a hole through the medial cortex 52.

As shown in FIG. 6 a screw 12 can now be inserted by a screw driver 66 to fix the stem 1 to the medial cortex 52. The procedure is repeated for the additional screws 12 inserted through the holes 11 of the stem 1 and engaging the medial cortex 52. Finally, screw 17 (FIG. 1) is driven into cancellous bone 18.

While the foregoing description and drawings represent the preferred embodiments of the present invention, it will be obvious for those skilled in the art that various changes and modifications may be made therein without departing from the true spirit and scope of the present invention.

I claim:

1. A femoral component for a hip joint prosthesis comprising an intramedullary stem having a free distal region, a proximal region extending to a neck for receiving a ball head, a medial side and a lateral side, said intramedullary stem having a longitudinal groove forming a U-shaped cross-section with said groove facing said lateral side and having screw holes extending from said lateral side to said medial side, and bone screws in said screw holes extending in the lateral to medial direction for fixation of said stem to the medial cortex, said bone screws having heads, and wherein said heads of said bone screws are lodged in said screw holes.

2. A femoral component according to claim 1 wherein at least said lateral side of each of said screw holes is adapted to permanently lock said head of said bone screws.

3. A femoral component according to claim 2, wherein at least said lateral side of said screw holes has a conical shape diminishing from said lateral side to said medial side.

4. A femoral component according to claim 1, wherein the depth of said groove is 5 to 50% of the total width of said U-shaped cross-section.

5. A femoral component according to claim 4, wherein the depth of said groove is 20 to 30% of the total width of said U-shaped cross-section.

6. A femoral component for a hip joint prosthesis comprising an intramedullary stem having a free distal region, a proximal region extending to a neck for receiving a ball head, a medial side and a lateral side, said intramedullary stem having screw holes extending from said lateral side to said medial side for receiving bone screws in the lateral to medial direction for fixation of said stem to the medial cortex, said bone screws having heads, wherein said heads of said bone screws are lodged in said screw holes, and a trochanteric collar extending from said proximal region of said stem in a lateral direction.

7. A femoral component according to claim 6 wherein said trochanteric collar has at least one screw hole for receiving at least one trochanteric bone screw.

\* \* \* \* \*